United States Patent
Best et al.

(10) Patent No.: US 12,383,737 B2
(45) Date of Patent: Aug. 12, 2025

(54) SKIN TREATMENT DEVICE WITH THERMALLY MODULATED HEAD

(71) Applicant: NSE Products, Inc., Provo, UT (US)

(72) Inventors: Richard R. Best, Mapleton, UT (US); Dale G. Kern, Hyde Park, UT (US)

(73) Assignee: NSE Products, Inc., Provo, UT (US)

( * ) Notice: Subject to any disclaimer, the term of this patent is extended or adjusted under 35 U.S.C. 154(b) by 418 days.

(21) Appl. No.: 17/833,559

(22) Filed: Jun. 6, 2022

(65) Prior Publication Data

US 2022/0395684 A1 Dec. 15, 2022

Related U.S. Application Data

(60) Provisional application No. 63/209,916, filed on Jun. 11, 2021.

(51) Int. Cl.
*A61N 1/32* (2006.01)
*A61F 7/00* (2006.01)
*A61N 1/04* (2006.01)
*A61N 1/36* (2006.01)

(52) U.S. Cl.
CPC .......... *A61N 1/328* (2013.01); *A61N 1/0476* (2013.01); *A61N 1/36031* (2017.08); *A61N 1/36034* (2017.08); *A61F 2007/0052* (2013.01); *A61F 2007/0075* (2013.01)

(58) Field of Classification Search
CPC ............. A61N 1/328; A61F 2007/0052; A61F 2007/0071
See application file for complete search history.

(56) References Cited

U.S. PATENT DOCUMENTS

| 5,601,618 A | 2/1997 | James |
| 7,182,776 B2 | 2/2007 | Grahn et al. |
| 7,559,907 B2 | 7/2009 | Krempel et al. |
| 9,545,523 B2 | 1/2017 | Nanda |
| 9,974,684 B2 | 5/2018 | Anderson et al. |
| 10,046,160 B1 | 8/2018 | Kern |
| 10,080,428 B2 | 9/2018 | Kern |
| 10,661,072 B2 | 5/2020 | Kern et al. |

(Continued)

FOREIGN PATENT DOCUMENTS

| WO | 2010009150 A1 | 1/2010 |
| WO | 2010091008 A1 | 8/2010 |

(Continued)

OTHER PUBLICATIONS

Design U.S. Appl. No. 29/819,521, filed Dec. 15, 2021, 39 pages.

(Continued)

*Primary Examiner* — Kaitlyn E Smith
(74) *Attorney, Agent, or Firm* — Dorsey & Whitney LLP

(57) ABSTRACT

A skin treatment device is provided with a thermally modulated treatment head adapted for contact with a user or other subject's skin. The device includes one or more thermal elements adapted to modulate the temperature of the head, a power source adapted to provide current to the thermal elements, and a controller adapted to modulate the head temperature by controlling the current delivered to the thermal elements. A topical agent can be disposed between the treatment head and the subject's skin, where the temperature of the topical agent is modulated in response to the temperature thereof.

23 Claims, 11 Drawing Sheets

(56) References Cited

U.S. PATENT DOCUMENTS

| | | | |
|---|---|---|---|
| 10,722,395 | B2 | 7/2020 | Weber et al. |
| 10,772,473 | B2 | 9/2020 | Johnstone et al. |
| 2004/0127895 | A1 | 7/2004 | Flock et al. |
| 2012/0239122 | A1 | 9/2012 | Dong et al. |
| 2014/0303608 | A1* | 10/2014 | Taghizadeh ............... A61F 7/00 606/20 |
| 2017/0105869 | A1 | 4/2017 | Frangineas |
| 2020/0383827 | A1 | 12/2020 | Weber et al. |
| 2021/0308452 | A1 | 10/2021 | Kern et al. |

FOREIGN PATENT DOCUMENTS

| | | | |
|---|---|---|---|
| WO | 2010098784 | A1 | 9/2010 |
| WO | 2017223417 | A1 | 12/2017 |

OTHER PUBLICATIONS

U.S. Appl. No. 63/256,106, filed Apr. 29, 2022, 138 pages.
International Search Report and Written Opinion dated Oct. 17, 2022 in connection with International Patent Application No. PCT/US2022/032372, 16 pages.

\* cited by examiner

SKIN TREATMENT DEVICE WITH THERMALLY MODULATED HEAD

CROSS-REFERENCE TO RELATED APPLICATIONS

The application claims priority to U.S. Provisional Patent Application No. 63/209,916, SKIN TREATMENT DEVICE WITH THERMALLY MODULATED HEAD, filed Jun. 11, 2021, which is incorporated by reference herein, in the entirety and for all purposes.

FIELD

The application relates to skin treatment. More generally, the application relates to skin treatment systems, devices, and methods with a thermally modulated treatment head. Suitable applications include, but are not limited to, microcurrent devices for cosmetic skin care and skin treatment, skin treatment systems with a thermally modulated head adapted for heating a topical agent, and combinations thereof.

BACKGROUND

The skin is the largest organ of the human body, forming a physical barrier to the environment and providing important functions including insulation, temperature regulation and protection against microorganisms, as well as touch, heat sensitivity, and other forms of sensation. The skin also regulates the passage of water and electrolytes, and produces vitamin D.

The outermost skin layer or epidermis covers the body's surface. Most of the epidermal cells are keratinocytes, which form an environmental barrier and synthesize vitamin D. The epidermis also includes melanocytes, which produce melanin to protect against harmful UV radiation, Merkel cells, which provide sensitivity to touch, and Langerhans cells, a type of white blood cell or macrophage that is part of the immune system, acting to protect the body against infection.

The epidermis surrounds the dermis. The structure of the dermis is provided by fibroblasts, which synthesize collagen and elastin proteins to form the extracellular matrix, with collagen fibers to provide strength and toughness, and elastin threads or filaments to provide elasticity and flexibility. The fibroblasts also produce proteoglycans, viscous proteins that provide hydration and lubrication, and regulate ionic binding and molecular transport. The dermis also includes macrophages and mast cells, part of the immune system, as well as the hair follicles, sweat and oil glands, nerve cells, and blood vessels.

The epidermis and dermis make up the cutis. Subcutaneous tissue connects the cutis to the underlying muscle and fascia, and to other connective tissue including the periosteum (covering the bones). The subcutis also includes elastin and adipose (fat) cells.

Skin firmness and elasticity are often associated with the production of Type I collagen (typically the more abundant form), as well as elastin, proteoglycans, and other components of what is known as the extracellular matrix. A healthy extracellular matrix can also improve skin resilience and coloration, and promote immune response.

A range of personal skin care products have been provided to help enhance these effects, including topical products and hand-held devices for cleansing, exfoliating and smoothing the outer skin layers. In galvanic systems, one or more anode or cathode electrodes are typically arranged to produce an electric potential across the skin, providing current flow through the epidermal and dermal layers. Advanced microcurrent based devices can include a control circuit operably connected to the electrodes, in order to carefully regulate the current to promote ion transport and other biological effects; e.g., as described in for example as described in U.S. Pat. No. 10,046,160 B1, U.S. Pat. No. 10,080,428 B2, U.S. Pat. No. 10,661,072 B2, and U.S. Pat. No. 10,772,473 B2, each of which is assigned to NSE (Nu Skin Enterprises) Products, Inc., of Provo Utah, and incorporated by reference herein.

More generally, skin response to electric current flow involves a number of complex and interacting biological processes, and the full range of different effects have not all been recognized in the prior art. There is an ongoing need more advanced approaches to skin care, including skin treatment techniques developed with a better understanding of the underlying biological response mechanisms of the skin, and how these mechanisms interact with different topical treatments and delivery techniques.

SUMMARY

A skin treatment device is provided with a thermally modulated treatment head adapted for contact with a user's skin. The device includes one or more thermal elements adapted to modulate the temperature of the head, a power source adapted to provide current to the thermal elements, and a controller adapted to modulate the head temperature by controlling the current delivered to the thermal elements. A topical agent can be disposed between the treatment head and the user's skin, where the temperature of the topical agent is modulated to have different temperatures in regions spaced from the skin surface, and proximate the skin surface.

In some examples, the device can be provided with one or more emitters or electrodes configured for electrical communication with the surface of the subject's skin. A voltage or current source can be adapted to generate an electrical waveform for application to the skin surface, via the one or more emitters or electrodes. A controller can be configured for modulating the electrical waveform, so that the pulse width, pulse period, pulse frequency and/or pulse amplitude vary in a periodic, random, pseudorandom, non-repeating or aperiodic manner.

DETAILED DESCRIPTION

Figure 1A:
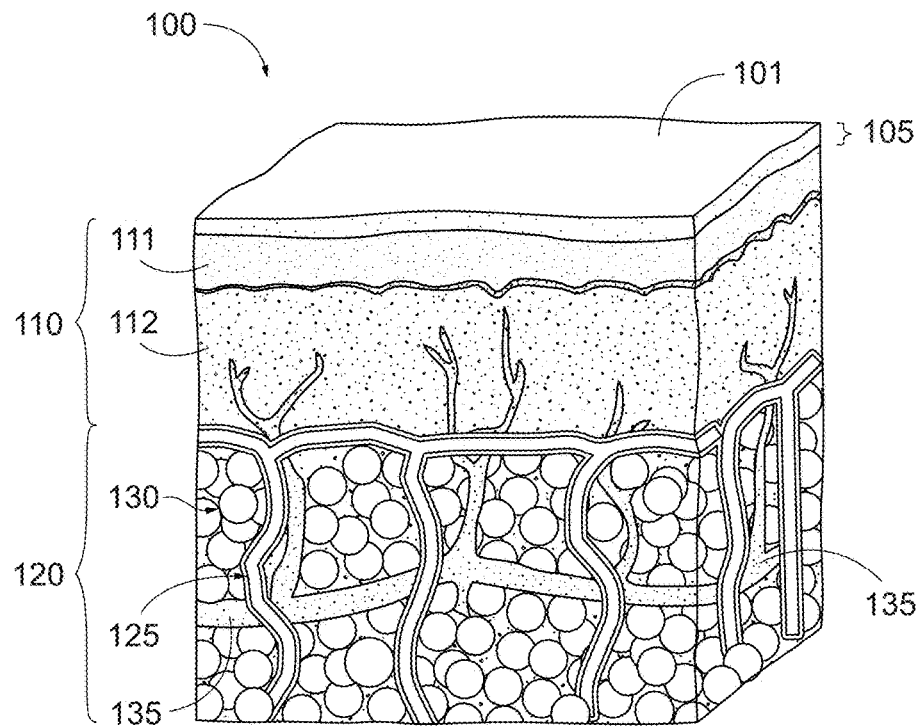
FIG. 1A is a sectional diagram illustrating representative components of human skin.

FIG. 1A is a sectional diagram illustrating representative structural and functional components of human skin 100. As shown in FIG. 1A, the skin (or "cutis") 100 includes an upper epidermal layer (or epidermis) 105 extending from the skin surface 101 to a lower dermal layer (dermis) 110. Together, the epidermis 105 and dermis 110 make up the cutaneous tissue or skin. The subcutaneous tissues comprise the subcutis (or hypodermis) 120, underlying the cutis 100.

Collagen fibers 125 extend from the lower dermis 110 through the subcutis 120, forming bands and sheets of connective tissue (fascia) connecting the skin (cutis) 100 to the underlying muscles and connective tissue. The dermis 110 also includes a papillary layer 111 and a reticular layer 112, formed of more loosely arranged and denser collagen fibers, respectively.

The subcutis 120 includes adipose tissues 130, for example in the form of lipocytes (fat cells) and intracellular or intercellular lipids, which can form lobules and other structures between the collagen fibers 125. A network of small blood vessels or capillaries 135 provide circulation, extending from the subcutis 120 into the dermis 110.

Figure 1B:
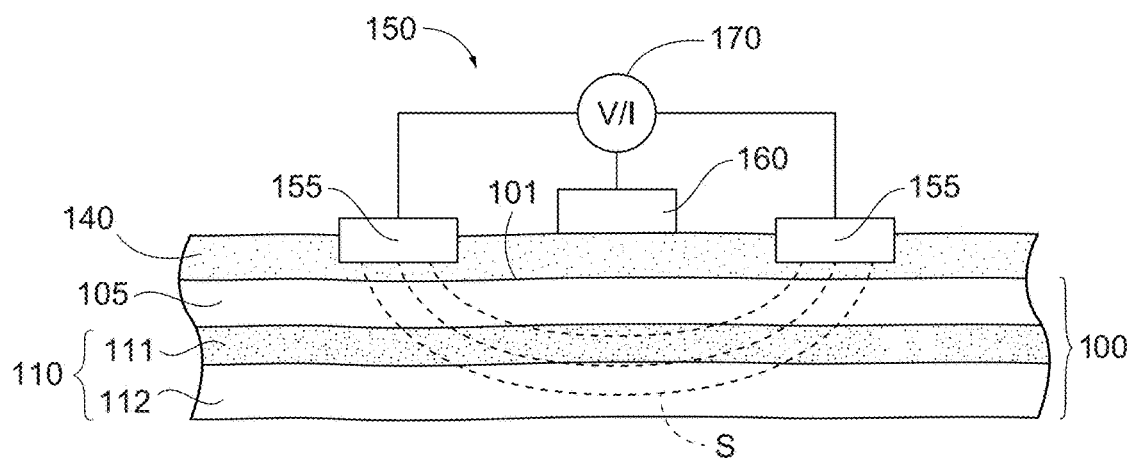
FIG. 1B is a sectional diagram illustrating a topical skin treatment.

FIG. 1B is a sectional diagram illustrating an electrical stimulus S applied to a skin surface 101, and propagating through different layers of the skin or cutis 100. A fluid, paste, gel or other topical skin treatment agent 140 can be applied to the skin surface 101; e.g., to improve conductivity, and to provide the skin 100 with moisturizes, nutrients and other beneficial agents.

For example, in one embodiment a current or microcurrent stimulus S can be generated by a skin treatment device 150 with one or more emitters or electrodes 155 disposed along the skin surface 101, either in direct contact with the skin surface 101, or in electrical contact with the skin surface 101 via a conducting topical agent 140. One or more thermal control components 160 can also be provided, in order to modulate the temperature of the topical agent 140 during application.

A current source or waveform generator 170 can be configured to generate a potential (V) or current (I) waveform for application to the skin surface 101 via one or more of the emitters or electrodes 155. It is also possible to use other forms of electromagnetic energy as a form of stimulus S to treat the skin 100, for example in the form of radio frequency (RF), infrared (IR), optical or ultraviolet (UV) light (e.g., low-energy near UV light), or to provide an energetic stimulus S in the form of sonic, subsonic or ultrasonic acoustic energy.

These energetic stimuli can be presented to the skin 100 as a modulated waveform, similar to the modulated waveforms provided in the form of an electrical or current stimulus S. Thus, electrical, electromagnetic and acoustic forms of energy are all within the teachings of the present disclosure, and any suitable combination of these energetic stimuli can be presented in the form of a modulated waveform.

In particular examples, one or more resistive heating elements or thermal control component ("thermal components") 160 can be used to heat the topical agent 140, adjacent the skin surface 101. On a molecular scale, the transfer and movement of molecules within the topical agent 140 increases with temperature. Heating can also activate ingredients in the agent 140, and allow active ingredients to more rapidly move through the agent 140, across the skin surface 101, and into the epidermis 105, and/or the (upper) papillary layer 111 and (lower) reticular layer 112 of the dermis 110. Heating may also reduce the viscosity of the topical agent 140 (e.g., in gel or fluid form), which will reduce the drag on the skin as the skin treatment device or head is moved over the skin. Using one or more thermal components 160 to modulate the temperature of the topical agent 140, heat from the fluid can also be transferred across the skin surface 101, increasing user comfort by providing a warming sensation, and opening pores in the skin to improve cleansing and absorption of active elements in the agent 140.

As shown in FIG. 1B, for example, an electrical stimulus S can be generated by applying a potential V (or current source I) between two or more emitters or electrodes 155, spaced along the outer surface 101 of the skin 100, either adjacent to or in direct contact with the skin surface 101. Alternatively, one or more electrodes 155 may be disposed on or adjacent the skin surface 101 in a particular location, for example on the face, arm, torso or leg, with another electrode 155 coupled remotely, for example via contact with the hand of the user (or other treatment subject), or elsewhere on the subject's body. In other applications, the electrical stimulus S can be applied with a single electrode 155; e.g., by applying an ungrounded (floating) potential waveform from one or more electrodes 155 to the skin surface 101, or by forming a current loop through the subject's feet or other ground contact.

Depending upon application, a potential V can be provided to the emitters or electrodes 155 to apply a current stimulus S to the top epidermal layer 105 of the skin 100, or a current propagating through the epidermal layer 105 to one or both of the papillary and reticular layers 111, 112 of the dermis 110. The electrical stimulus may also propagates into or through the subcutis 120, promoting a favorable response from both cutaneous and subcutaneous tissues. The stimulus S can thus promote a range of biological responses in epidermal, dermal (cutaneous) and subcutaneous tissues. Alternatively one or more (or all) of the emitters or electrodes 155 can take the form of LEDs or laser light sources (or other electromagnetic emitters) configured to provide a stimulus in the form of RF, IR, optical or UV light energy, or one or more acoustic transducers configured to provide a subsonic, sonic, ultrasonic, or other acoustic stimulus, or any suitable combination of electrical, acoustic, and electromagnetic emitters 155.

Suitable waveforms and waveform modulation techniques are described, for example, in U.S. Publication No. 2021/0308452 A1, "Modulated Waveform Treatment Device and Method," and in U.S. Provisional Patent Application No. 63/256,106, "Current Control System for Skin Treatment Device," filed Oct. 15, 2021, each of which is incorporated by reference herein, in the entirety and for all purposes. In particular applications, for example, pulse width modulation (PWM) can be used to generate the stimulus S as a pulsed microcurrent waveform, or other energetic stimulus S, for example by applying a programmed, random or pseudorandom pulse width modulated (PRPWM) current or voltage waveform, or as a modulated electromagnetic or acoustic waveform, as described herein. The power output to the skin surface can also be modulated to reduce transients and increase user comfort, while maintaining treatment efficacy.

In other examples, a DC (direct current) or pulsed DC potential V or current I is applied via the electrodes 155, so that the electrical stimulus S propagates in a particular direction through the skin 100. In other examples, an AC (alternating current) potential V of current I can be applied, so that the electrical stimulus S propagates back and forth, in alternating fashion.

The potential V can be applied as a steady-state (constant or alternating) voltage signal, or using a modulated waveform. Depending on application, the pulse width, amplitude, period and frequency of the applied voltage V or current I can all be controlled, either individually or in combination, in order to generate the electrical stimulus S as an AC, DC or pulsed DC current treatment for the skin 100 of the user or other subject.

Figure 2:
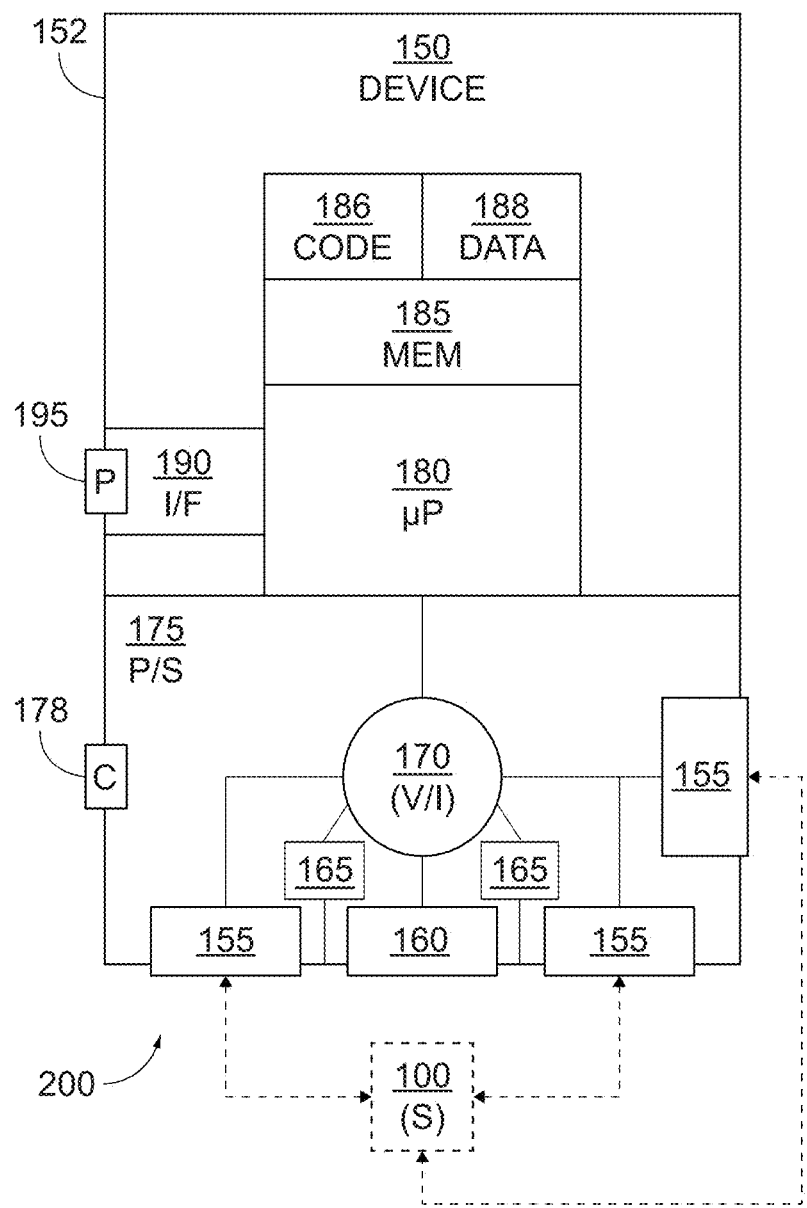
FIG. 2 is a block diagram of a skin treatment device with thermally modulated treatment head.

FIG. 2 is a block diagram of a representative skin treatment apparatus, system or device 150 disposed within a housing 152, with a treatment head 200 configured for thermal modulation during delivery of a microcurrent based skin treatment or other energetic stimulus S; e.g., according to FIG. 1B. As shown in FIG. 2, one or more electrodes or other emitters 155 are disposed on the treatment head 200; e.g., extending from the bottom surface of the housing 152. One or more thermal components 160 are provided to modulate the temperature of the treatment head 200 (and any adjacent topical) during delivery of the stimulus to the skin 100, with a current or voltage waveform generator 170 and a power source or power supply 175 adapted for application of the stimulus S via one or more of the emitters or electrodes 155, as described herein.

Depending on application, device 150 can also a microprocessor (μP) based controller 180 with memory 185, and a power supply (P/S) 175 adapted for operation of the electrodes 155, thermal components 160, waveform generator 170 and controller 180. The microprocessor controller 180 is provided in data communication with memory 185, which provides storage for control code 186 and operational data 188.

The power supply 175 can be provided in the form of a line connection or a rechargeable capacitor or battery system, for example with a power port or charger (C) 178 adapted for external wired or wireless (e.g., inductive) charging of the power supply 175. A communications interface (UF) 190 can be adapted for data and control communications with the controller 180, for example using a hard-wired or wireless communications port (P) 195.

In operation of device 150, power supply 175 provides power to the electrodes 155 via the voltage or current waveform generator (or source) 170, as well as the thermal components 160, sensors 165, controller 180, memory 185, interface 190, and the other internal components of device 150. Controller 180 is configured regulate the potential (V) or current (I) waveform generated by source 170, for example by executing control code 186 stored in memory 185. Control parameters and other operational data 188 can be used for modulating the waveform provided to each selected emitter or electrode 155, in order to deliver the desired amplitude, frequency, and pulse width modulation. One or more sensors 165 can also be provided in direct or indirect contact with the treatment head or skin surface, for example in direct physical contact with the treatment head or skin surface, or in inductive, conductive or thermal communication. Sensors 165 can be configured to measure treatment head and skin surface temperature and resistivity, and to determine other skin conditions such as hydration level, skin firmness, etc. Suitable sensors 165 can also be provided to measure or monitor environmental conditions such as ambient temperature and humidity, etc.

The microprocessor controller 180 can also be adapted to monitor feedback signals from the emitters or electrodes 155, and for regulating the applied potential (V) or current (I) responsive to the feedback. Feedback-based regulation allows the controller 180 to maintain the desired electrical stimulus S, taking into account the number and arrangement of electrodes 155 as well as the subject's skin type and related skin conditions such as resistivity, temperature, hydration, etc., for example as determined with additional data from one or more skin sensors and other environmental sensors 165. The controller 180 can also be adapted to regulate the current stimulus S transmitted through the subject's skin via the electrodes 155, based on the based the voltage (V) or current (I) waveform generated by the source 170, and based on operational and environmental conditions such as the temperature of the skin surface (or topical agent disposed on the skin surface), the impedance of the skin between adjacent electrodes 155, and other operational data include prior (recent or historical) treatment information recorded in the operational data 188.

Generally, this disclosure is directed to the value of heating technology in skin treatment devices, and more specifically to heating technology focused on the topical agent or composition applied to the subject's skin surface (e.g., as a fluid or gel medium). On a molecular scale, the warmer the topical composition, the more rapid the transfer and movement of molecules within the topical medium. Heating can allow active ingredients to more rapidly move through the fluid or gel medium, while reducing the medium's viscosity.

Warming the topical agent to a suitable temperature thus reduces drag between the skin surface and the treatment device, as it moves over the subject's skin. A warmer topical composition can also transfer thermal energy to the skin, providing a beneficial warming sensation and opening pores in the skin surface, to increase penetration of active ingredients.

This approach contrasts with existing technologies, including warming the topical fluid when pumped or otherwise dispensed from a reservoir. This approach requires combining a fluid pump with a heating element, and topical agents that are pre heated before application can quickly cool, and the benefits of heating can be lost within a few seconds. Heating the entire treatment surface, on the other hand, requires high amounts of energy, and can lead to discomfort.

Figure 3:
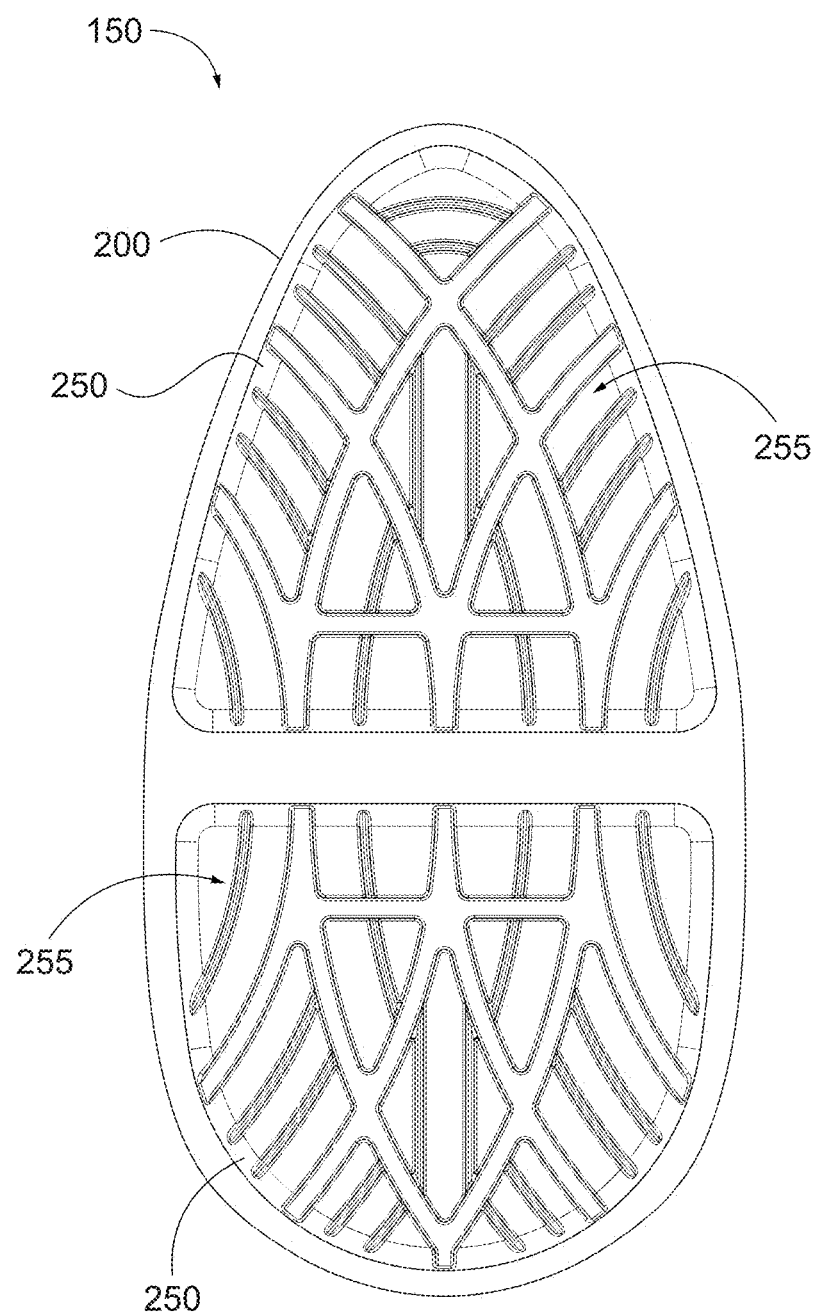
FIG. 3 is a plan view of a thermally modulated head for a skin treatment device.

FIG. 3 is a plan view of a thermally modulated head 200 for a skin treatment device; e.g., according to device 150 of FIG. 2, or another suitable skin treatment system or apparatus. As shown in FIG. 3, head 200 include two skin contact elements 250, which are provided with ridged, grooved or other textured or patterned application surfaces 255 adapted for application of a skin treatment or other topical fluid to the user's skin (or to the skin of another subject, by the user). In galvanic and microcurrent-based systems, contact elements 250 are typically provided in the form of emitters or electrodes 155, as describe above with respect to device 150, and adapted for application of the topical fluid by electro-osmosis electrophoresis, iontophoresis, and other electrochemical techniques, for example as described in U.S. Pat. No. 10,046,160 B1, which is incorporated by reference herein.

As shown in FIG. 3, for example, skin contact elements 250 can be formed as heated metal plates, or other conducting elements, which also allow for a microcurrent treatment to be applied to the skin surface. The application surfaces 255 can also be heated to deliver the topical agent in a temperature range selected for use comfort, viscosity, and mobility of active agents, for example from about 37 C to about 42 C, or up to a preselected maximum upper limit selected for user comfort; e.g. up to about 45 C.

Simple, direct heating mechanisms can be used to heat the topical agent to the selected temperature range, as described herein, for example with a minimum power output of about 15.6 W, distributed over one or more a treatment surfaces 250 with an area of about 60 to 80 $cm^2$ or more. Alternatively the thermal power output and treatment surface area may vary; e.g., from less than about 10 W to about 15-20 W, 20-25 W or more, over a treatment area up to about 50 $cm^2$, from about 50-100 $cm^2$, or more. The thermal power output can also be adapted to heat the topical to a desired temperature within a particular time, for example within a minute or less, when the agent is distributed over the treatment area with the device in a static location adjacent the subject' skin. The heating time may also vary, for example from about 30 seconds (or less) to about two minutes (or more), and the thermal power output can also be adapted to maintain the desired topical agent temperature when the device is subject to dynamic movement over the skin surface.

Figure 4A:
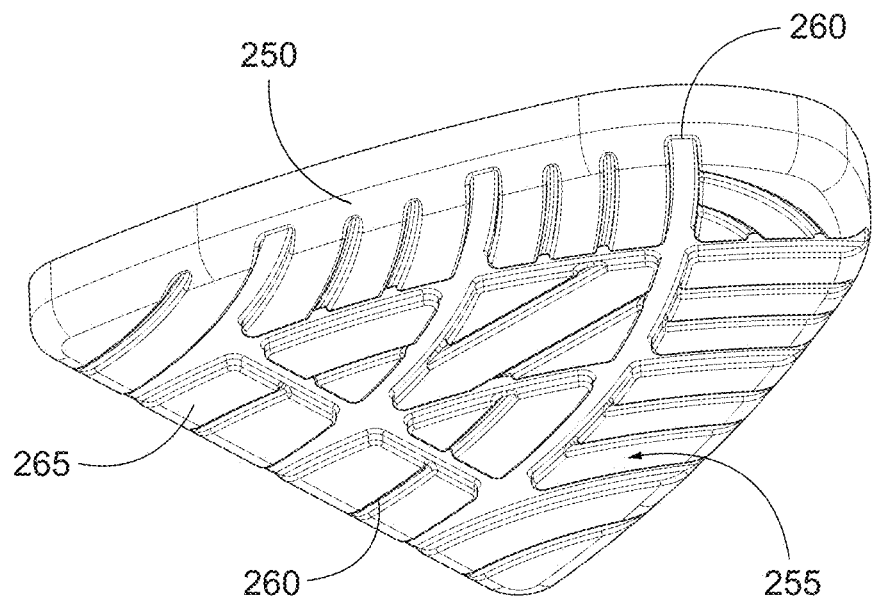
FIGS. 4A and 4B are isometric views of first and second contoured, thermally modulated skin contact elements for a treatment head.
Figure 4B:
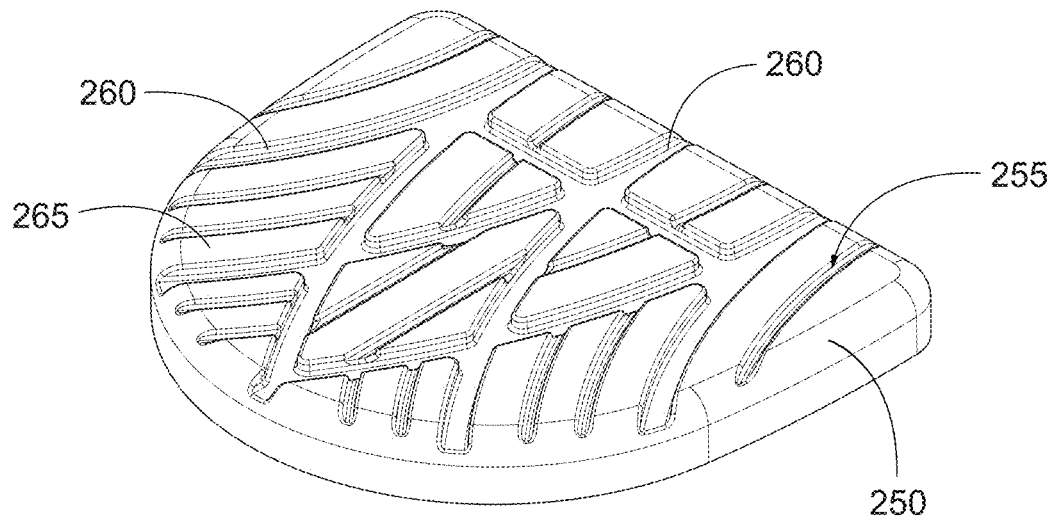

FIGS. 4A and 4B are isometric views of first and second contoured, thermally modulated skin contact elements 250 for a treatment head. FIGS. 4A and 4B illustrate the grooved, ridged, or similarly textured or patterned application surfaces 255, as adapted for distribution the topical fluid over the subject's skin.

In some configurations, textured or patterned application surfaces 255 comprise a network of branching, intersecting, on interconnected groove or channel structures 260, in a proximal position with respect to the contact element 250 (spaced from the subject's skin), and a complementary network or set of oblong pads, lands, or similar structures 265, in a distal position with respect to the contact element 250 (adjacent the subject's skin). Alternatively, complementary ridged or grooved structures 260 and pads or lands 265 can be formed in parallel, intersecting, branched, concentric, or randomized patterns, or combinations thereof.

Contact elements 250 of FIGS. 4A and 4B can be defined with first and second (e.g., opposing polarities), selected to provide a microcurrent treatment to the adjacent skin surface. The individual application surfaces 255 are defined within the circumference of the device body or treatment head 200 (see FIG. 3), substantially flush with the bottom profile of the device, with textured features such as groves 260 and lands 265 are adapted for spreading (distributing) a topical agent when moved across the skin surface.

Contact elements 250 can be made from stainless steel, nickel, copper, chrome, silver, and alloys thereof, or other suitable conducting metals or metal alloys. The application surfaces 255 can be formed in a punch and die operation (e.g., from stamped metal plate contact elements 250), or via a plating process, machining, or a combination thereof. Contact elements 250 can also be formed with substantially smooth application surfaces 255, or with grooves or channels 260 and ridges or lands 265 defining rounded nodules, undulating ridges, crossed perpendicular bars, ovals, circles, rectangular or oblong features, triangles, stars, or other textured or patterned geometries, as adapted for a range of different skin treatments and topical applications.

Figure 5A:
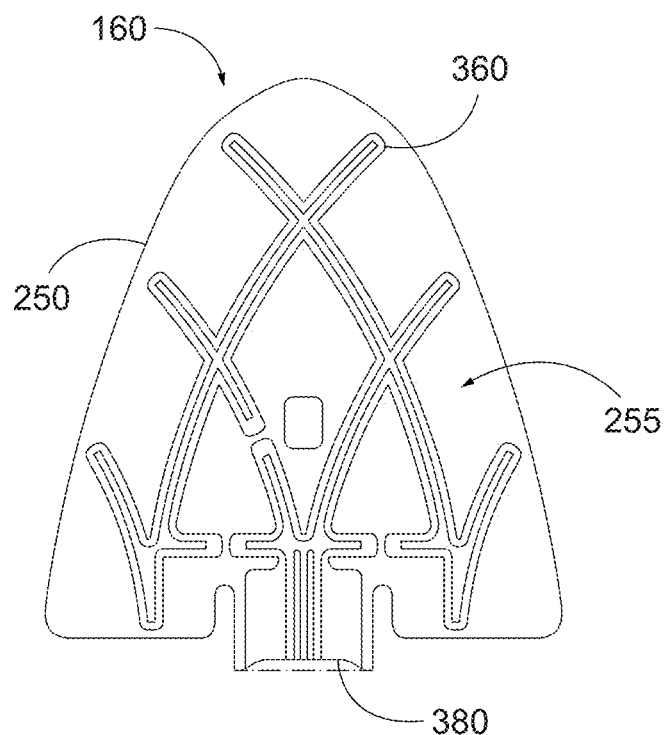
FIGS. 5A and 5B are plan views of representative thermal elements for a treatment head.
Figure 5B:
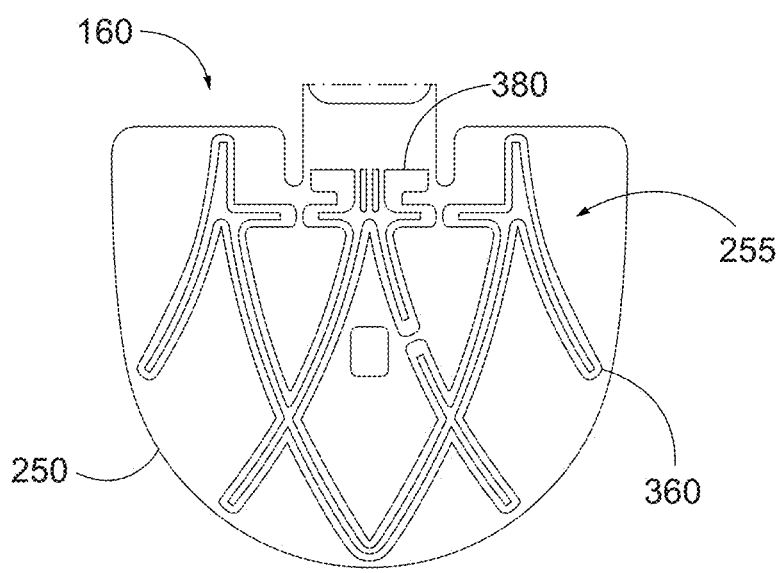

FIGS. 5A and 5B are plan views of a representative thermal control component 160 with individual thermal elements 360 for modulating the temperature of a skin treatment head, for example with first and second skin contact elements 250 according to FIGS. 4A and 4B. In this particular example, thermal elements 360 comprise a set of interconnected, substantially linear or lineal segments, conforming to the grooved structure of the skin contact surfaces on the opposite side of each respective contact element 250. Connectors 380 are provided to connect the thermal elements 360 together with a rechargeable battery or other suitable power source.

Figure 6:
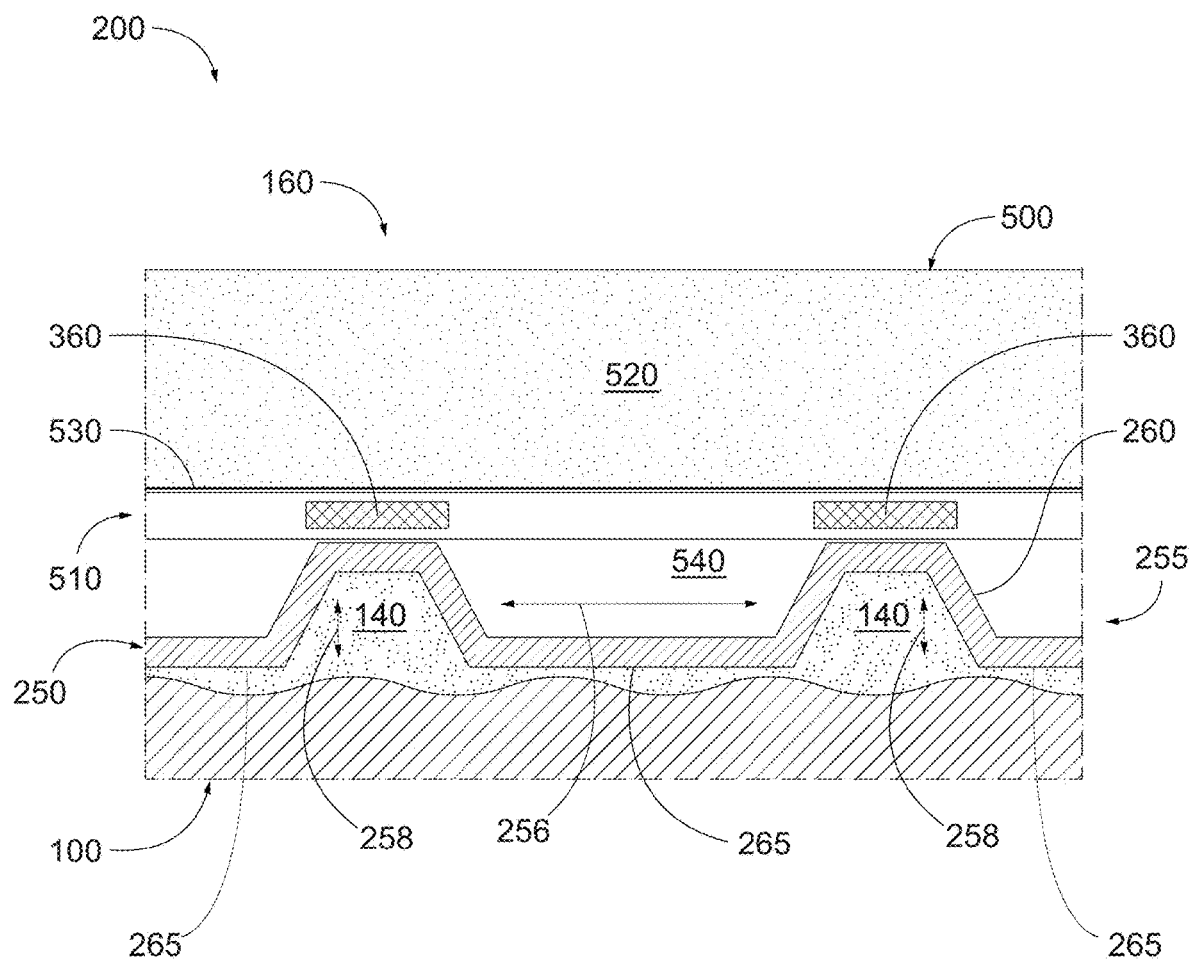
FIG. 6 is a cross-sectional view of a thermally modulated skin treatment head, showing the thermal elements.

FIG. 6 is a cross-sectional view of a thermally modulated skin treatment head 200, illustrating a thermal component 160 configured as a heating module 500 with one or more individual thermal elements 360. In this configuration, the thermal elements 360 can be embedded in a polymer, polyimide, silicon or similar material 510, forming a pad-like modular heater structure 500. The heating module 500 can also be provided with thermal insulation 520 and a foil reflector 530, or other thermally reflective and insulating elements configured to direct heat generated by thermal elements 360 toward through the adjacent skin contact element 250, and into the topical gel, fluid or other topical agent 140 adjacent the subjects skin 100.

In some configurations, thermal elements 360 are disposed adjacent and along the individual ridges, grooves or channel structures 260 making up the proximal portions of the patterned application surface 255, spaced from the user's skin 100. Air gaps or similar insulating spaces 540 are defined between the heating module 500 with thermal elements 360, and the distal portions or lands 265 of the application surface 255, adjacent the user's skin 100.

Thermal elements 360 are energized by a power supply and controlled by a microprocessor, for example a power supply 175 and a processor-based controller 180, provided in combination with other components of a skin treatment device 150 according to FIG. 2. One or more thermocouple sensors or other suitable temperature-sensitive elements 165, can be utilized to determine the temperature of the contact element 250 at any or all locations along the application surface 255, in order to provide feedback to the controller 180, and to maintain a desired temperature profile 256 along or across the contact surface 255, defining a thermal grant 258 in the adjacent topical agent 140.

In some applications, thermal elements 360 comprise resistive heating elements adapted to modulate the temperature of the contact element 250 (e.g., a thermally conducting metal plate), adjacent the topical agent 140 being delivered to the user's skin along the ridged, grooved or channel structures 260. Generally, increasing the temperature of the topical agent 140 will increases the fluid conductivity, and increased fluid conductivity can provide increased ability to deliver active components (e.g., molecular ions), in response to electrochemical effects such as iontophoresis, electro-osmosis and electrophoresis.

In some examples, heating of the topical agent 140 can be concentrated in the grooves or channels 260 adjacent the thermal elements 360, and through which the topical fluid flows for delivery to the subject's skin 100. Limiting heating to the channels 260 can increase efficiency for heating the topical agent 140 (e.g., as opposed to the subject's skin 100), resulting in lower energy demand on the power supply.

Depending on skin type, topical composition, and individual preference, a typical comfort range for the temperature of a topical agent 140 when applied to a subject's skin 100 may be in the range of up to 37-42 C, or up to a comfort limit of about 45 C. Depending upon the design of thermal elements 360 and the size of the treatment head 200, the may be achieved with a power output of about in the range of about 10-20 W, for example about 15.6 W, to produce a desired temperature range on the skin contact element 250, for example after about one minute of operation, or after a few minutes of operation, or less than a minute of operation. Is some examples, this power level range may also be suitable to maintain the desired head and fluid temperature ranges, as the topical agent 140 is delivered along channels 260 while the treatment head 200 is moved across the subject's skin 100. In these applications, suitable rechargeable power sources are can provide a treatment cycle in the range of a few minutes or more, for example five to ten minutes, or more or less.

In some examples, the contact surface 45 is formed of a metal or similar thermally and electrically conducting material, for example by stamping. In other examples, the head 200 can be built with a metal or similar thermally conductive material along the channels 260 adjacent the thermal elements 360, and other portions of the contact element 250 adjacent the skin 100 may be formed of thermally and/or electrically insulating materials, for example using a two-piece metal/plastic or composite contact element 250, or other suitable multi-component form.

Suitable contact elements 250 can be formed with different components having different thermal conductivities, or with a substantially uniform conducting material. Suitable thermal elements 360 can be operated to modulate the temperature of the contact elements 250 at different positions along the treatment head 200; maintaining a temperature profile 256 between the individual thermal elements 360 disposed along the treatment surface 255. For example, the temperature profile 256 can be controlled to define a thermal gradient 258 between the proximal ridge or groove structures 260, spaced from the subject's skin 100, and the lands or similar distal portions 265 of the textured or patterned treatment surface 255, adjacent the subject's skin 100. The temperature profile 256 can be controlled as the head 200 moves across the skin 100, in response to heat absorption through the skin 100, at the nominal skin temperature. Further, the thermal gradient 258 can be generated using a either one-component contact element 250 (e.g., with a metal co0ntact surface 255), or two-component design (e.g., a metal stamped channel structure 260, with plastic or composite skin contact material in the distal or land portions 265, adjacent the skin 100).

In some of these applications, the temperature of the topical agent 140 in channels 260 may increase to about 50-55 C, or up to 60 C, in order to increase activation chemistry in active treatment components of the agent 140. Activation chemistry can be very sensitive to temperature, and the treatment components of topical agent 140 can be activated at higher temperature (e.g., up to 60 C) in the channels 260, spaced from the skin 100, then delivered to skin at lower (more comfortable) application temperature range, along the pads or lands 265 adjacent the skin 100.

In addition to ionization, increased fluid temperature can also affect molecular structure (e.g., resulting in the release of active ingredients in a "caged" molecular structure, or by releasing one or more active topical components that react readily at relative higher fluid temperature in the grooves 260, adjacent the thermal elements 360 and spaced from the subject's skin 100, and then are applied to the skin 100 at relatively lower fluid temperatures along the lands or pads 265, adjacent the skin 100.

In other examples, thermal elements 360 can be provided as a combination or resistive heating and Peltier devices or similar elements 360 adapted to heat one or more skin contact elements 250, or regions within a given element 250, and to cool one or more other contact elements 250, or other regions within a given element 250. This arrangement can be used to enhance the thermal gradient 258 in the topical agent 140 between the subject's skin 100 and the channels 260, spaced from the skin 100. This arrangement can also be used to modulate the temperate of one or more contact elements 250, or different regions within a given element 250, so that the subject experiences different temperatures along or adjacent different pads or lands 265, as the treatment head 200 moves across the skin 100.

Generally, the use of heating channels or other structures 260 to introduce a thermal gradient 258 in the topical agent 140 provides for a more advanced approach to topical skin treatment, defining an in-situ reaction chamber to activate the topical agent 140 at one temperature, and deliver agent 140 to the skin 100 at another temperature. The thermal gradient 258 can be defined to heat the agent 140 to a higher temperature for activation, and to lower the temperature of the agent 140 for application to the skin 100.

Single or multiple skin contact pads or similar elements 250 can be used in a given head 200. The substantially linear or lineal thermal elements 360 can also be replaced with "buttons" or other discrete structures, or with a resistive plate. One or more regions of the treatment head 200 could also be uniform in temperature profile, or comprise a combination of different heated or temperature modulated regions and unheated or unmodulated regions, with textured, patterned or smooth application surfaces 255. For example, the head 200 can be provided with regions of the contact element 250 heated to a temperature range selected to open pores and encourage vasodilation, and other regions cooling to a temperature range selected to close pores and encourage vasoconstriction, while promoting iontophoretic delivery and enhanced permeability for active skin treatment components in the topical agent 140.

Figure 7A:
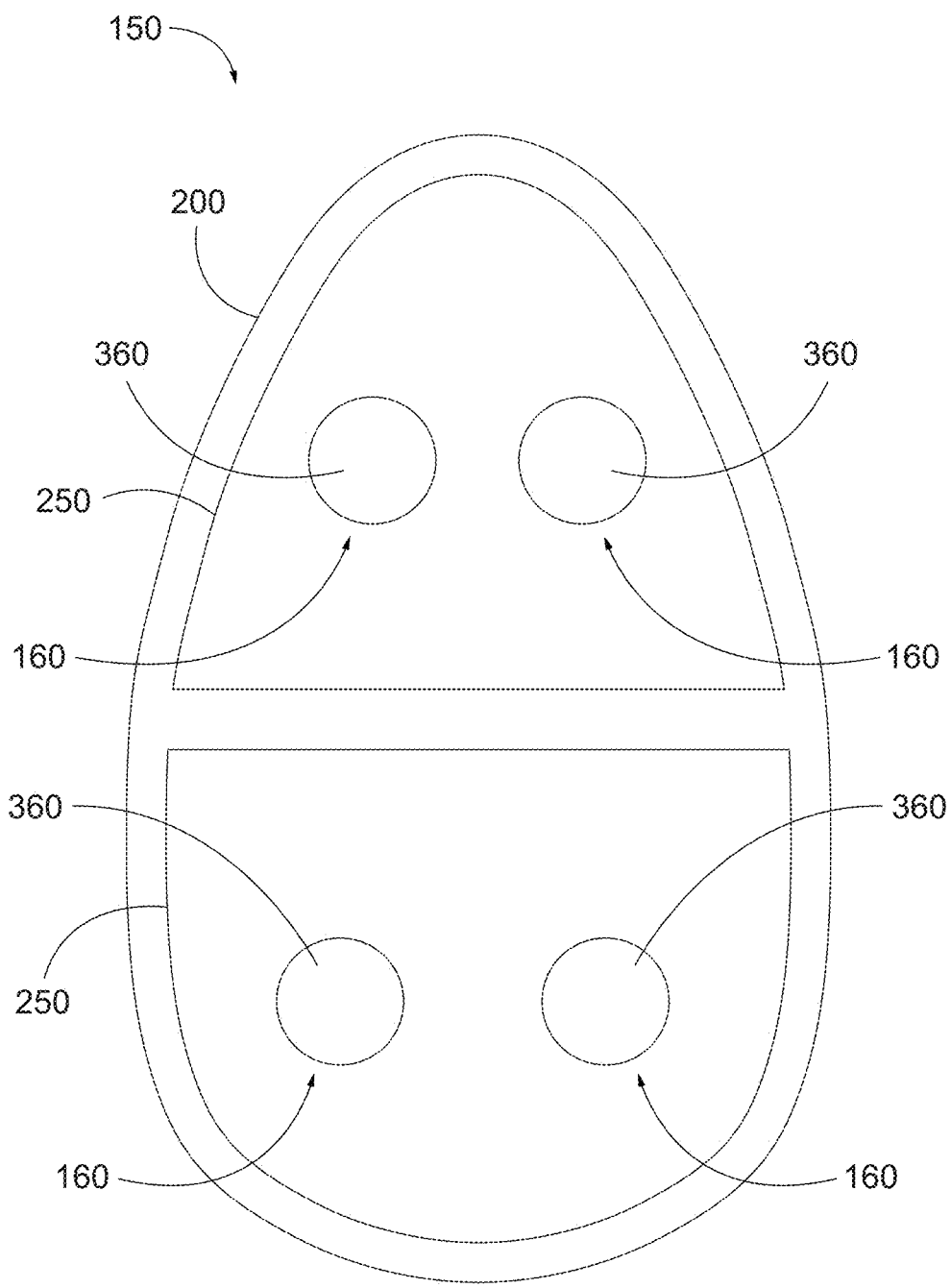
FIGS. 7A and 7B are alternate plans view of a thermally modulated skin treatment head, illustrating alternative thermal element configurations.
Figure 7B:
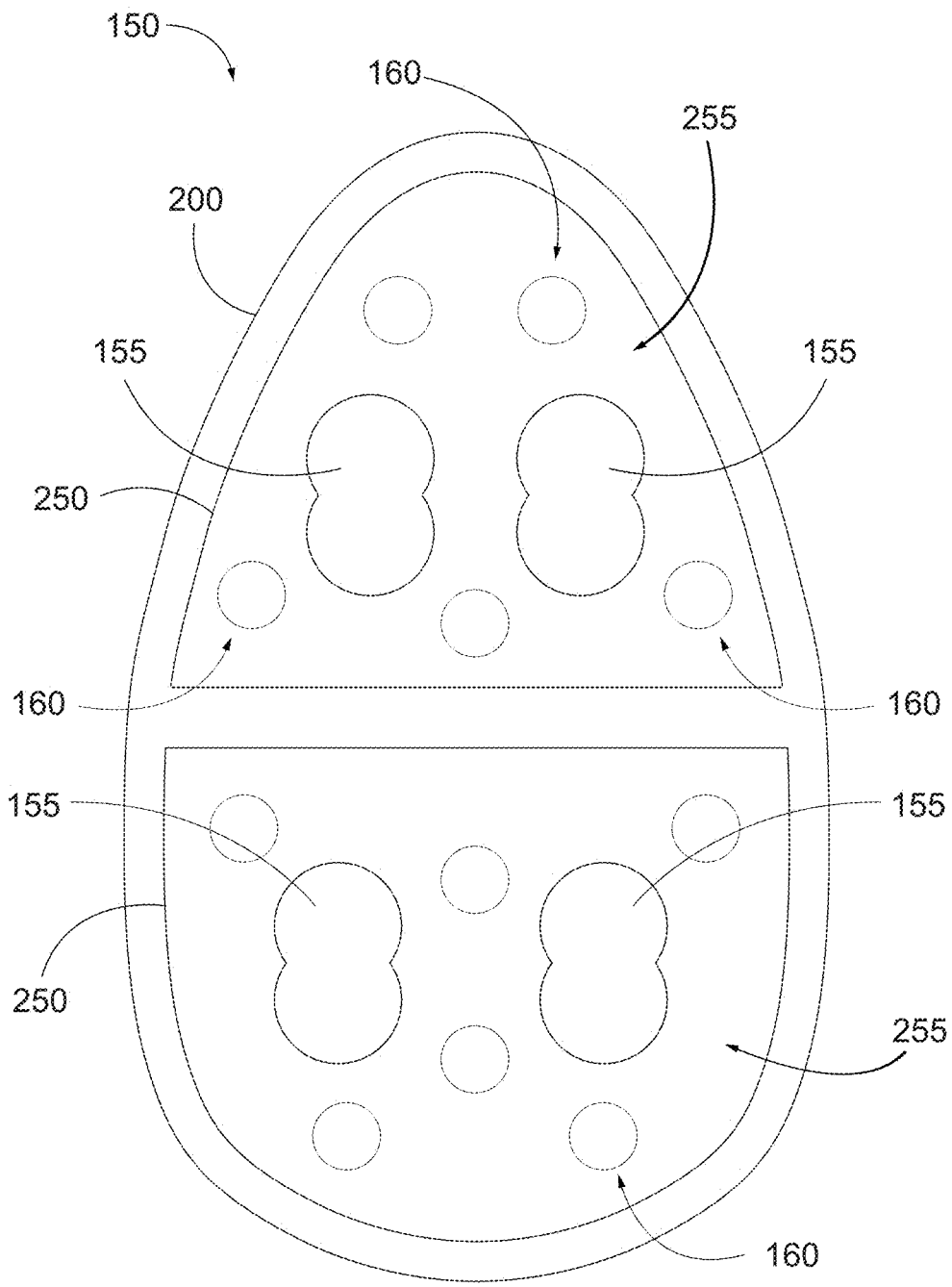

FIGS. 7A and 7B are alternate plan views of a thermally modulated treatment head 200 for a skin treatment device 150, illustrating different configurations for the thermal control components 160. In the example of FIG. 7A, thermal components 160 are provided in the form of one or more "buttons" or similar discrete elements 360; e.g., disposed on the upper (interior) surface of the contact element 250, inside the housing of device 205, and opposite the textured or patterned application surface, which is adjacent the subject's skin. Alternatively, oblong, rectangular, oval, or continuous-plate elements 360 can be used.

FIG. 7B shows a plan view illustrating the application surface 255 of a skin treatment device 150, on the outer side of the contact element 250, adjacent the skin surface, and opposite the view of FIG. 7A. As shown in FIG. 7B, application surface 250 can incorporate one or more substantially round, semi-spherical, or elongate, lobed emitters or electrodes 155; e.g., as described in U.S. Design patent application Ser. No. 29/819,521, "Skin Treatment Device," filed Dec. 15, 2021, which is incorporated by reference herein. In these examples, one, two or more pairs of electrodes 155 can be provided on contact element 250, and operated at opposite polarities to deliver a microcurrent treatment to the adjacent skin surface.

One or more thermal components 160 can be incorporated into the textured or patterned application surface 250 adjacent the electrodes 155, for example in the form of discrete thermal elements 360 disposed on the opposite side of the application surface 250, inside the housing of device 150, as shown in FIG. 7A, and spaced from the skin surface with the respect to the electrodes 155. Alternatively, one or more thermal components 160 can be disposed within the electrodes 155, or in other locations along the contact surface 205, in any of the other configurations described herein.

Figure 8A:
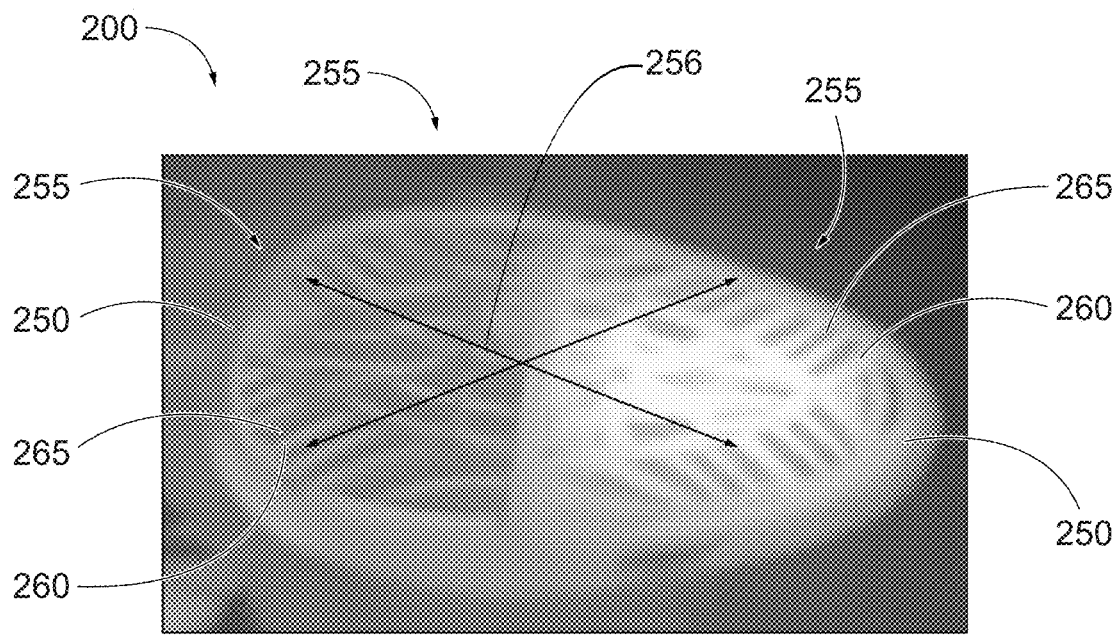
FIG. 8A is a thermal image or heat map of a thermally modulated skin treatment head.

FIG. 8A is a thermal image or heat map of a thermally modulated skin treatment head 200, illustrating a three-dimensional temperature profile 256 defined along or across the textured or patterned application surface 255. As shown in FIG. 8A, the temperature profile 256 is defined both between the two skin contact elements 250, and between different textured or patterned regions of each individual application surface 255. In this particular example, the temperature tends to be relatively higher in the front contact element 250 (right side of image), as compared to the back contact element 250 (left side of image).

In addition, the temperate profile 256 may tend to be relatively higher proximate the grooved structures 260, spaced from the skin surface, and relatively lower proximate the pads or lands 265, adjacent the skin surface. This defines a thermal gradient in the adjacent topical agent; e.g., as achieved by selected placement of the thermal elements to increase temperature-dependent chemical activity for the topical agent in the grooves 260, spaced from the skin surface, and a relatively lower temperature proximate the lands or 265, where the topical agent is in contact with the subject's skin.

Figure 8B:
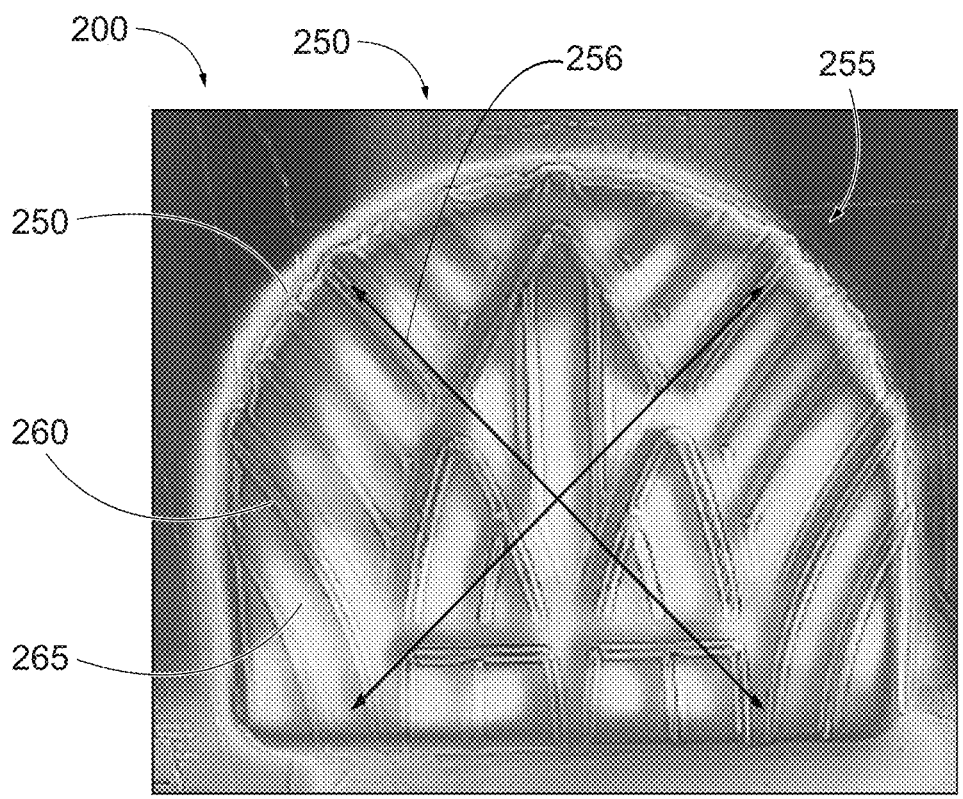
FIG. 8B is a thermal image or heat map of a thermally modulated skin contact element.

FIG. 8B is an alternate thermal image or heat map of a skin treatment head 200 with a thermally modulated skin contact element 250, illustrating the temperature profile 256 between different regions of the textured or patterned application surface 255. In this example, the orientation of the skin contact element 250 is reversed, with heat distributed via a flat conducting plate (e.g. a solider copper plate or similar conducting element) disposed on the back side of the application surface 255, opposite the surface shown in FIG. 8B. As a result, the temperature profile 256 typically defines relatively higher temperatures proximate the lands or valleys 265, adjacent the heat plate, and relatively lower temperatures proximate the grooved or ridged structures 260, spaced from the heat plate.

Figure 9A:
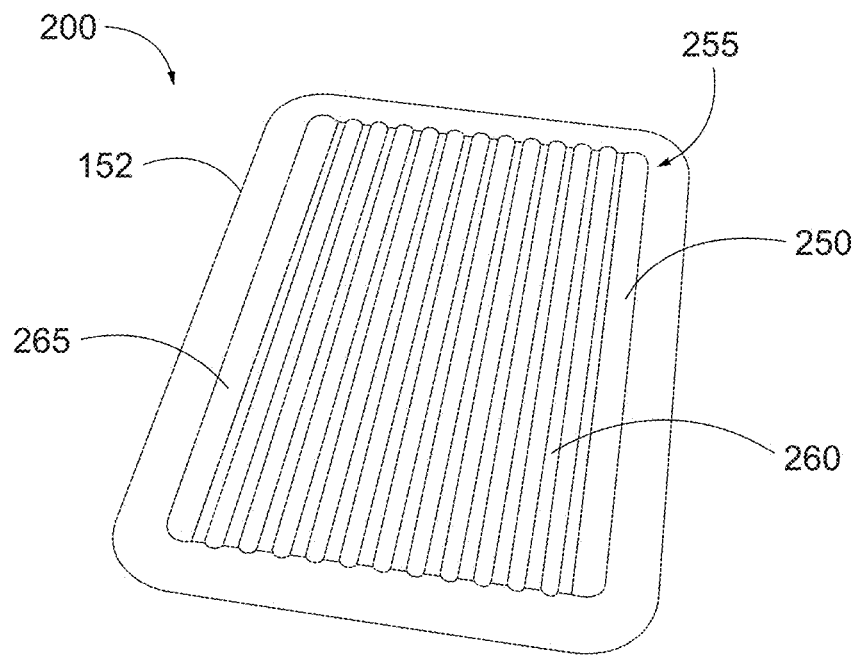
FIG. 9A is a perspective view of an alternate skin treatment head.

FIG. 9A is a perspective view of an alternate skin treatment head 200, in an oblong or rectangular configuration. In this example, the contact element 250 is disposed within a plastic, polymer or composite frame or housing 152. The contact element 250 is formed of a conducing metal material, with textured or patterned application surface 255 defined by a series of generally parallel grooves 260 and lands 265, with ridge-shaped lands 265 disposed between adjacent, complementary valleys or grooves 260.

In these examples, the contact element 250 can be formed as a corrugated metal stamping disposed within a plastic or composite frame 152. A heating element can be provided in the form of a laterally extended plate disposed on the opposite side of the contact element 250, adjacent the grooves 260 (spaced from the lands 265), or as a set of linear elements aligned along the grooves 260. Suitable heating elements include a thermocouple plate adapted to the shape of the contact element 250, and extending across the grooves 260, or a set of linear thermocouple elements extending along the individual grooves 260.

Figure 9B:
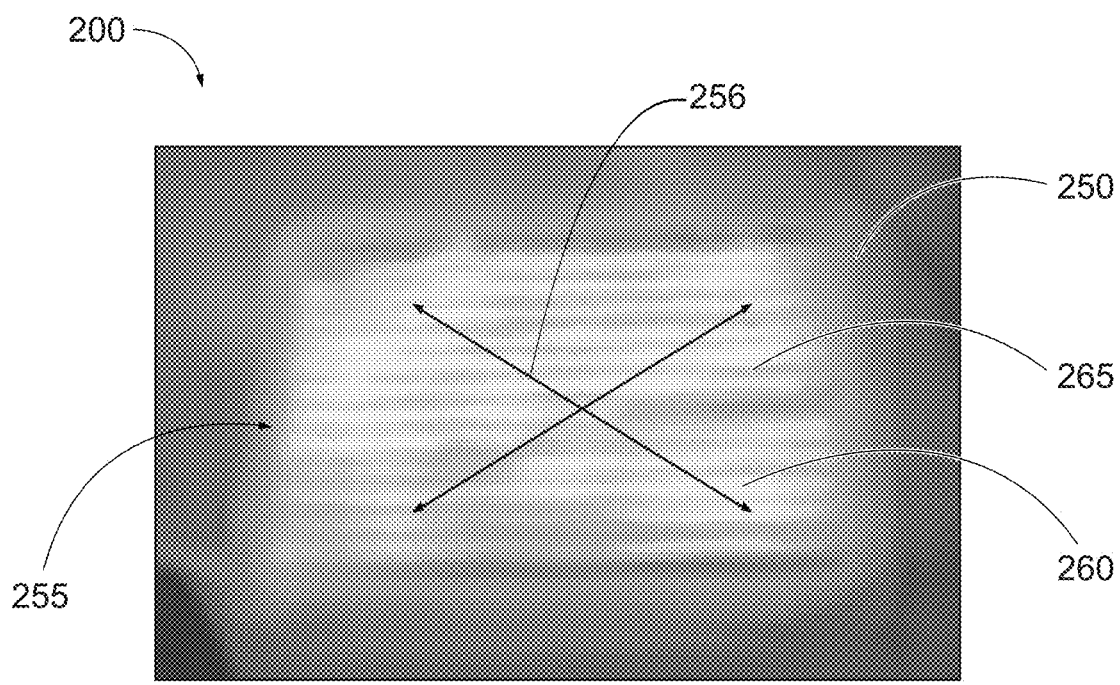
FIG. 9B is a thermal image or heat map of the skin treatment head in FIG. 9A.

FIG. 9B is a thermal image or heat map of the skin treatment head 200 and application and contact element 250 in FIG. 9A, illustrating a temperature profile 256 defining a thermal gradient between different regions of the textured or patterned application surface 255. As shown in FIG. 9B, the temperature profile 256 defines a thermal pattern across the application surface 255; e.g. when the heating element is turned on and the surface 255 is allowed to come to an equilibrium temperature. In this example, the temperature profile is generally higher toward or adjacent the grooves 260, which are proximate the heating element or elements on the back side, and spaced from the skin surface. The temperature profile is generally lower adjacent the ridges or lands 265, which are spaced from the heating elements, and proximate the skin surface.

Upon application of a topical agent, a thermal gradient is defined between portions of the topical agent adjacent the grooves 260, as compared to the lands 265. Generally, the heat pattern defines hotter spots (higher temperatures) along the grooves or channels 260, forming a warmed reservoir of topical agent for delivery to the subject's skin, with cooler spots (lower temperatures) along the lands 265, after the topical agent is applied the skin surface. The topical agent is applied by movement of the application surface 255 across the skin, distributing the topical by a wiping motion from which the topical flows from the grooves or channels 260 (warmer topical agent, spaced from the skin surface), and across the lands 265 (cooler topical agent, adjacent the skin surface).

Figure 10:
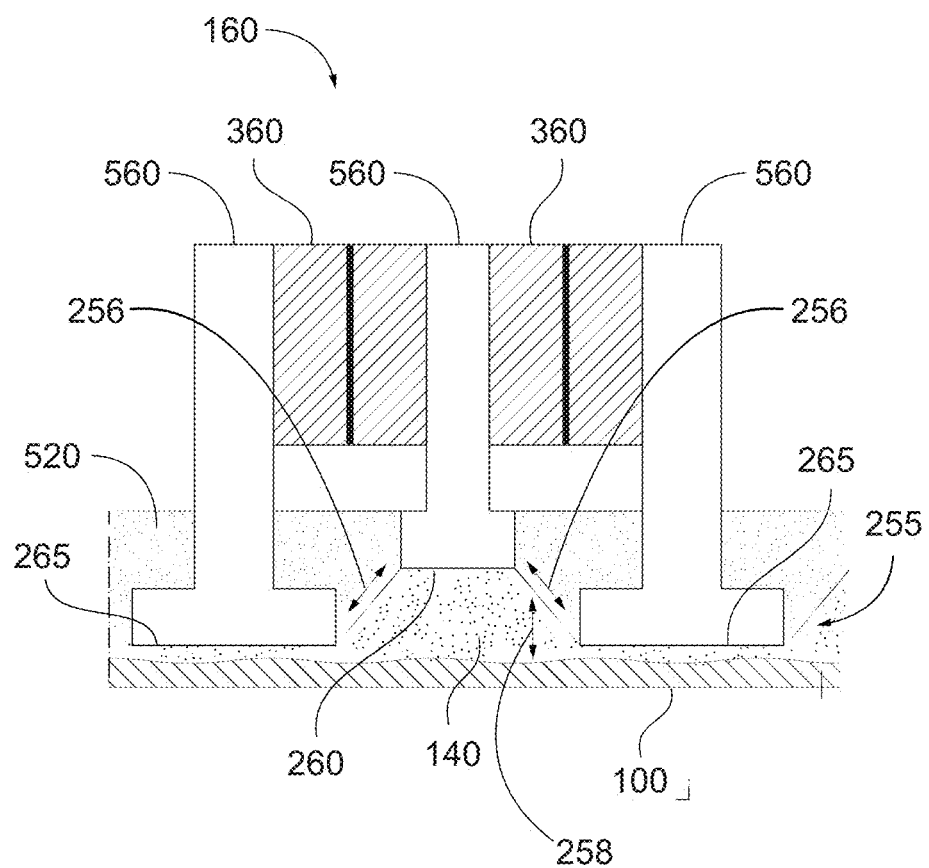
FIG. 10 is a cross sectional view of a thermally modulated skin treatment head, illustrating an alternate thermal element configuration.

FIG. 10 is a cross sectional view of a thermally modulated skin treatment head 200, illustrating an alternate configuration for the thermal control component 160. In this example, Peltier thermoelectric elements 360 are disposed between adjacent thermal conductors 560, with elongated configurations extending to the grooved portions 260 of the textured or patterned application surface 255, spaced from the skin surface, and contact pads or lands 265 adjacent the user's skin. Thermal insulation 520 is provided on exposed portions of the application surface 255, in order to direct heat toward the topical agent 140.

A topical agent 140 can be applied to the subject's skin 100. The thermal elements 360 are controlled to alternately cool and heat the conductors 560 on the adjacent, opposing sides of each element 360, providing a temperature differential adjacent the grooves 260 and lands 265. For example, the thermal elements 360 can be oriented to transfer heat from a first conductor 560 extending to a grooved portion 260 of the application surface 255, to another conductor 560 extending to a contact pad or land 265.

In this configuration, a temperature profile 256 is controlled along or across the application surface 255 to establish a thermal gradient 258 in the topical agent 140; e.g., so that the topical agent 140 is relatively warmer in and adjacent the grooves 260, spaced from the skin surface, and relatively cooler toward the contact pads or lands 265, adjacent the skin surface. Alternatively the direction of heat flow via elements 360 may be reversed, from the grooves 260 to the lands 265, so that the thermal gradient 258 defines the topical agent 140 at a relatively cooler temperature in and adjacent the grooves 260, spaced from the skin surface, and at a relatively warmer temperature toward the contact pads or lands 265, adjacent the skin surface.

This disclosure is made with respect to representative examples and embodiments. Each can be used either alone or in combination with any other embodiment or example described or illustrated herein, and each may incorporate additional modifications, changes, equivalents, and alternatives that fall within the breadth of disclosure, as read and understood by a person of ordinary skill, and without departing from practice of the invention as claimed. These various examples and embodiments are provided by way of illustration, and should not be construed to limit the scope of the invention, nor to limit the meets and bounds of coverage as defined by the language of the appended claims.

The invention claimed is:

1. A skin treatment device comprising:
   a thermally modulated treatment head coupled to a housing;
   one or more thermal elements adapted to generate a temperature profile across the treatment head;
   a power source adapted to provide current to the thermal elements; and
   a controller adapted to modulate the temperature profile by controlling the current delivered to the thermal elements;
   wherein the temperature profile defines different temperatures along different portions of the treatment head; and
   wherein the controller is adapted to modulate the temperature profile to define a relatively higher temperature along a first portion of the treatment head, spaced from an adjacent skin surface to which the treatment head is applied, and a relatively lower temperature along a second portion of the treatment head, proximate the skin surface.

2. The device of claim 1, where the temperature profile defines a thermal gradient for a topical agent disposed between the treatment head and an adjacent skin surface to which the treatment head is applied.

3. The device of claim 2, wherein the thermal gradient defines a relatively higher reaction temperature of the topical agent in a first region spaced from the skin surface, and a relatively lower application temperature of the topical agent in a second region proximate the skin surface.

4. The device of claim 1, further comprising one or more emitters or electrodes configured to apply an electromagnetic or current waveform to a skin surface adjacent the treatment head.

5. The device of claim 4, further comprising a voltage or current source adapted to generate the waveform for application to the skin surface via the one or more emitters or electrodes, wherein the controller is configured to modulate one or more of a pulse width, pulse period, pulse frequency or amplitude of the waveform in a periodic, random, pseudorandom, non-repeating or aperiodic manner.

6. The device of claim 4, wherein the one or more thermal elements are disposed adjacent the treatment surface inside the housing, spaced from the one or more emitters or electrodes along the treatment surface.

7. The device of claim 1, further comprising one or more thermal sensors adapted to generate temperature data responsive to the temperature profile at or along one or more locations on the treatment head, wherein the controller is configured to maintain or control the temperature profile responsive to the temperature data.

8. The device of claim 1, further comprising a textured or patterned application surface defined on the treatment head, and comprising one or more surface features adapted for application of a topical agent to an adjacent skin surface.

9. The device of claim 8, wherein the controller is adapted to modulate the temperature profile to maintain the topical agent at different temperatures in regions spaced from the skin surface, and proximate the skin surface.

10. The device of claim 8, wherein the thermal elements comprise one or more resistive elements disposed along or adjacent the textured or patterned application surface inside the housing, opposite the skin surface, and adapted to generate the temperature profile responsive to the current.

11. The device of claim 1, wherein the one or more thermal elements are disposed within the housing along or adjacent one or more grooves or recesses defined in the treatment head, and spaced from one or more ridges or lands defined adjacent or between the one or more grooves or recesses.

12. The device of claim 1, wherein the thermal elements comprise one or more Peltier devices configured to transfer heat from a first region of the treatment head to a second region of the treatment head, wherein:
   the first region is proximate a skin surface adjacent the treatment head and the second region is spaced from the skin surface, or
   wherein the first and second regions successively contact a skin surface responsive to motion of the treatment head across the skin surface.

13. A skin treatment method comprising:
   disposing a thermally modulated treatment head adjacent a skin surface, wherein one or more thermal elements are adapted to generate a temperature profile across the treatment head; and
   moving the treatment head across the skin surface, wherein the temperature profile is modulated to define different temperatures along different portions of the treatment head;
   wherein the temperature profile is modulated to define a relatively higher temperature along a first portion of the treatment head, spaced from the skin surface, and a relatively lower temperature along a second portion of the treatment head, proximate the skin surface.

14. The method of claim 13, further comprising applying a topical agent to the skin surface, wherein the temperature profile defines a thermal gradient in the topical agent with a relatively higher temperature in a region spaced from the skin surface, and a relatively lower temperature in a region proximate the subject's skin surface.

15. The method of claim 13, wherein an electromagnetic or current waveform is applied to the skin surface via one or more emitters or electrodes disposed on the treatment head.

16. The method of claim 15, wherein one or more of a pulse width, pulse period, pulse frequency or amplitude of the waveform is modulated in a periodic, random, pseudorandom, non-repeating or aperiodic manner.

17. The method of claim 15, wherein the one or more thermal elements are disposed adjacent the treatment surface inside the housing, spaced from the one or more emitters or electrodes along the treatment surface.

18. The method of claim 13, wherein the treatment head defines a textured or patterned surface having one or more surface features adapted for application to the skin surface.

19. A device comprising:
   a thermally modulated treatment head coupled to a housing, the treatment head comprising a treatment surface adapted for application to a skin surface;
   a pattern of grooves, channels, lobes or lands defined in the treatment surface;
   one or more thermal elements adapted for generating heat adjacent the pattern, wherein a temperature profile is defined across the treatment head;
   a power source adapted to provide current to the thermal elements; and
   a controller configured for modulating the temperature profile defined across the treatment surface by controlling current delivered to thermal elements;

wherein the temperature profile defines different temperatures along different portions of the treatment head, and along the pattern; and wherein the controller is adapted to modulate the temperature profile to define a relatively higher temperature along a first portion of the treatment head, spaced from an adjacent skin surface to which the treatment head is applied, and a relatively lower temperature along a second portion of the treatment head, proximate the skin surface.

20. The device of claim 19, wherein at least a portion of the skin contact surface is formed of an electrically conductive material adapted for current delivery to the skin surface.

21. The device of claim 19, wherein the pattern of grooves, channels, lobes or lands define flow structures adapted for application of a topical agent to the skin surface.

22. The device of claim 19, wherein the thermal elements comprise one or more resistive heating elements disposed along one or more of the grooves, channels, lobes or lands.

23. The device of claim 22, wherein the thermal elements are embedded in or disposed adjacent a layer of material configured to hold the resistive heating elements along the one or more of the grooves, channels lobes or lands, in spaced relation to one or more others of the grooves, channels, lobes or lands, said material being one or more of electrically insulating, thermally conductive, or thermally insulating.

* * * * *